United States Patent [19]

Krone et al.

[11] Patent Number: 5,229,469
[45] Date of Patent: Jul. 20, 1993

[54] BIOLOGICALLY DEGRADABLE POLYAMINO DICARBOXYLIC ACID—CO—ANHYDRO AMINO DICARBOXYLIC ACID DERIVATIVE

[75] Inventors: Volker Krone, Flörsheim; Axel Walch, Frankfurt am Main, both of Fed. Rep. of Germany

[73] Assignee: Hoechst Aktiengesellschaft, Frankfurt am Main, Fed. Rep. of Germany

[21] Appl. No.: 651,295

[22] Filed: Jan. 29, 1991

[30] Foreign Application Priority Data

Jan. 31, 1990 [DE] Fed. Rep. of Germany ....... 4002736

[51] Int. Cl.$^5$ .............................................. C08G 69/48
[52] U.S. Cl. .................................. 525/420; 424/78.22; 424/78.37; 525/419; 528/328
[58] Field of Search ................ 525/420, 419; 528/328

[56] References Cited

U.S. PATENT DOCUMENTS

| | | | |
|---|---|---|---|
| 3,297,033 | 1/1967 | Schmitt et al. | 128/335.5 |
| 3,371,069 | 2/1968 | Miyamae et al. | 260/78 |
| 3,773,919 | 11/1973 | Boswell, Jr. et al. | 424/19 |
| 3,927,204 | 12/1975 | Neri et al. | 424/78 |
| 4,069,307 | 1/1978 | Higuchi et al. | 424/22 |
| 4,093,709 | 6/1978 | Choi et al. | 424/19 |
| 4,180,646 | 12/1979 | Choi et al. | 528/153 |
| 4,304,767 | 12/1981 | Heller et al. | 424/78 |
| 4,356,166 | 10/1982 | Peterson et al. | 424/19 |
| 4,906,473 | 6/1990 | Bader et al. | 424/426 |

FOREIGN PATENT DOCUMENTS 0274127 7/1988 European Pat. Off. .

OTHER PUBLICATIONS

Neri et al., "Synthesis of α,β-Poly[(2-hydroxyethyl)-DL-aspartamide] a New Plasma Expander," J. of Med. Chem., 1973, vol. 16, No. 8 pp. 893–897.
Neri et al., "α,β-Poly(2-Hydroxyethyl)-DL-Aspartamide," Macromolecular Syntheses, vol. 8, pp. 25–28.
Rosen et al., "Bioeradible polyanhydrides for controlled drug delivery," Biomaterials, 1983, vol. 4, Apr., pp. 131–133.
Kenny, "Evaluation of Sodium Poly-α, L-glutamate as a Plasma Expander," Proc. Soc. Exp. Biol. Med. 100, 1959, pp. 778–780.

Primary Examiner—Harold D. Anderson
Attorney, Agent, or Firm—Finnegan, Henderson, Farabow, Garrett & Dunner

[57] ABSTRACT

The invention relates to biologically degradable polymers, in particular polyaminodicarboxylic acid-co-anhydroaminodicarboxylic acid derivatives, to a process for their preparation and to the use thereof for depot preparations having controlled delivery of active compound.

3 Claims, No Drawings

BIOLOGICALLY DEGRADABLE POLYAMINO DICARBOXYLIC ACID—CO—ANHYDRO AMINO DICARBOXYLIC ACID DERIVATIVE

The invention relates to biologically degradable polymers, in particular polyaminodicarboxylic acid-co-anhydroaminodicarboxylic acid derivatives, a process for their preparation and the use thereof for depot preparations having controlled delivery of active compound. The active compounds are embedded in a matrix consisting of the polymers according to the invention and released in a controlled manner in vivo by bioerosion of the matrix. During the degradation of the products according to the invention, fragments which are endogenous or known in their biotolerability are predominantly formed and are metabolized by natural metabolic means or excreted by the kidneys as a result of their water solubility.

A modern drug treatment requires, in particular for the administration of active compounds, novel administration forms which combine a controlled delivery rate of the active compounds with high biocompatibility of the depot. A long-lasting controlled delivery of active compound is of great relevance because of the increasing importance of chronic diseases and long term-orientated treatment concepts in human and veterinary medicine. Biodegradable polymers are particularly advantageous as matrix materials for depot systems of this type, as the bioerosion controls the release of active compound and makes the surgical removal of a depot of this type unnecessary.

Drug delivery systems in which the active compound is dispersed in a non-degradable polymer matrix and released by diffusion are described in U.S. Pat. No. 4,069,307. However, after exhaustion of the active compound reservoir such implants have to be removed from the organism surgically.

In biologically degradable drug delivery systems, as indicated in U.S. Pat. No. 4,093,709, the active compound is dispersed in a biodegradable polymer which releases the active compound on degradation. Typical biologically degradable polymers investigated by the prior art are homo- and copolyesters, in particular of lactic and glycolic acid, such as are described in U.S. Pat. Nos. 3,773,919 and 3,297,033. A disadvantage is, inter alia, the low or poorly controllable swellability of the polyesters in physiological medium, which prevents the transport of the active compounds incorporated in the implant through the polymer matrix to the surface and effects only a slow release rate after an initial "burst effect".

More recently, polyacetals and polyketals (U.S. Pat. No. 4,304,767) or polyanhydrides (H. G. Rosen et al., Biomaterials 131 (1983) and polyorthoesters (U.S. Pat. No. 4,180,646) have been described, which were developed as biologically degradable polymers for use as implant materials.

As a further class of polymers, polyamides, in particular poly-α-L-amino acids, have been described in U.S. Pat. No. 3,371,069 as bioabsorbable implant materials. However, the industrial production of polyamino acids requires the use of expensive protected amino acids, relatively large amounts of highly toxic phosgene, the removal of the protecting groups and the subsequent derivatization of the polymers obtained.

A further disadvantage of polyamides of this type is the presence of charged groups as a result of incomplete derivatization during the synthesis of the implant material. The pure poly-L-glutamic acid and pure poly-L-lysine mentioned in the patents are toxicologically extremely hazardous (A. D. Kenny, Proc. Soc. Exp. Biol. Med. 100, 778 (1959)) and their copolymers formed by biodegradation of hydrophobic derivatives must therefore also be very critically evaluated.

U.S. Pat. No. 4,356,166 describes biodegradable implant materials which release a bioactive compound in vivo. Progestins which are first chloroformylated and then covalently bonded to the polymer are described as bioactive compounds in U.S. Pat. No. 4,356,166. Poly(-hydroxyalkyl)-L-glutamine or poly(hydroxyalkyl)-L-aspartamide are employed here as polymers. The bioactive compounds are either bonded via a so-called "spacer group" or else directly via the reactive component of the polymer. The release rate of the bioactive compound is controlled by means of the molecular weight of the polymer or by means of the length and the character of the "spacer group".

A disadvantage of the substances according to U.S. Pat. No. 4,356,166 is that they are already pharmaceuticals with high pharmacological activity themselves. In such polymer/active compound conjugates (polymeric drugs), biocompatible polymer and active compound form a unit whose properties are determined in a complex manner by both components. The release rate of the polymer-immobilized bioactive molecule is variable in the context of the abovementioned parameters, but crucially dependent on the nature of the active compound. Hydrophobic bioactive substances such as, for example, steroid hormones, can only be cleaved from the polymer backbone very slowly in aqueous biological medium and are therefore suitable exclusively for extreme long-term depot forms. Novel polymer/active compounds conjugates must be synthesized for each active compound, which extremely restricts the utility of the concept of polymer-immobilized pharmaceuticals described in U.S. Pat. No. 4,356,166.

For these reasons, these substances are not suitable for use as polymers which are degradable in a controlled manner and which release an active compound as a result of their own biodegradation, the active compound being embedded in the inert polymer matrix without being bonded chemically to the polymer.

A substantial improvement has already been achieved by the biodegradable poly(hydroxyalkyl)-aminodicarboxylic acid derivatives which are described in EP 0,274,127. However, even these biodegradable polymers still have the following disadvantages:

a) The microparticles prepared using these substances are only suspensible in water using auxiliaries. The use of auxiliaries such as ®Pluronic or dextrans, however, is not unproblematic as these auxiliaries pass into the organism during the implantation of the active compound depot.

b) In aqueous medium, microparticles of this type have a tacky, oily consistency which leads to an agglomeration of the individual particles.

c) The release profile of the active compound from these microparticles—using some poly(hydroxyalkyl)-aminodicarboxylic acids according to EP 0,274,127—still always shows a considerable "initial burst", i.e. an initially very high release rate of active compound, which then very rapidly decreases.

d) The degradation times determined in vitro for microparticles according to EP 0,274,127 (phosphate buffer, 37° C.) are too long—in particular for use as an active compound depot for peptide active compounds.

The object of the present invention was to develop polymers which have the advantages described in EP 0,274,127, but without having to accept the above-mentioned disadvantages.

Polyaminodicarboxylic acid-co-anhydroaminodicarboxylic acid derivatives (polyaminodicarboxylic acid-co-AHADA derivatives) have now been synthesized which are surprisingly outstandingly suitable for use as degradable drug implants having controlled active compound delivery. The active compounds are in this case not bonded chemically to the polymer, but only embedded in this polymer matrix. The degradation rate of the polymer in vivo and thus, at the same time, the release rate of the active compound can be controlled in the desired manner by incorporation of suitable biologically inactive groups. In particular, the suspensibility in water of the microparticles prepared using the polymers according to the invention and their consistency can be improved by the incorporation of unopened anhydroaminodicarboxylic acid rings (AHADA rings). Additionally, the release profile and the degradation time is further improved. The advantage of this procedure is that now those active compounds can also be administered over a relatively long period at a relatively constant dose which can either be not bonded chemically to a polymer at all or else are too sensitive to survive the very drastic conditions during the chemical coupling to the polymer. Moreover, the polymers can fundamentally be employed universally as a pharmacologically inert matrix for all relevant pharmaceuticals, independently of the molecular size and other physicochemical parameters. The fact that it was possible to further improve the properties of the polymer according to EP 0.274,127 by the incorporation of unopened AHADA rings is therefore particularly surprising, as the tackiness of the polymers and the poor suspensibility of the microparticles according to EP 0,274,127 is obviously based on the hydrophilicity and the manifestation of hydrogen bridges in the main polyamide chains or in the amide-containing side groups. However, the AHADA units remaining in the copolymers according to the invention are at least just as capable of the manifestation of hydrogen bridges as the main polyamide chain or the amide-containing side group. However, the "rigid" character of the AHADA units unexpectedly predominates, which led to solid products which were also non-oiling in water. The particles also hardly agglomerate in water, so that suspending auxiliaries can be entirely dispensed with. The outstanding consistency of the copolymers according to the invention is also shown in the relatively problem-free spraying to give microparticles.

Active compound-containing microparticles composed of these copolymers also show a further substantial advantage in release measurements: there is nearly no "initial burst", i.e. no strongly increased release of active compound in contact with water in the first hours.

The more rapid "degradation times", which can be put down to a more rapid reaction or dissolution in water (<4 weeks in phosphate buffer at 37° C.), also fits in well with use as an active compound depot for peptide active compounds which are intended to be largely released within 4 weeks.

The copolymeric products according to the invention are additionally economical, as the first stage of the synthesis only has to be partially further reacted. These biologically degradable polymers are obtained by polycondensation of aminodicarboxylic acids, which are then partially reacted with water, amino alcohols, ammonia or alcohols to give polyaminodicarboxylic acid-co-AHADA derivatives and are then reacted, if desired, with carboxylic acids, carbonyl halides or haloformic acid esters in a polymer-analogous acylation to give further polyaminodicarboxylic-co-AHADA derivatives according to the invention. In vivo, these polymers are metabolized to give non-toxic, non-allergenic and non-immunogenic compounds and excreted.

The invention thus relates to: polyaminodicarboxylic acid-co-anhydroaminodicarboxylic acid derivates of the formula I

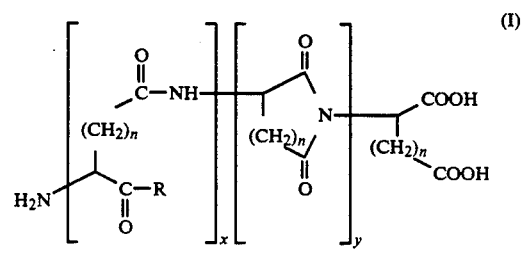

in which
n is 1 or 2,
x is 1 to 500,
y is 1 to 500, where
x+y is 2 to 1000 and
R is $O-R^1$ or $NH-R^2$, in which $R^2$ is H, $(CH_2)_m-OR^1$, $(CH_2)_m-O-C(O)-R^1$ or $(CH_2)_m-O-C(O)-OR^1$ and m is 2 to 6 and R is H, aryl, aralkyl, arylalkenyl, alkyl or $C_3-C_8$-cycloalkyl or a biologically inactive steroid alcohol or an amino acid, where aryl is unsubstituted or substituted by $C_1-C_4$-alkyl, $C_2-C_4$-alkenyl, $C_1-C_4$-alkylcarbonyloxy, $C_1-C_4$-alkoxycarbonyl, $C_1-C_4$-alkoxy or hydroxyl, where said alkyl radicals for $R^1$ have 1-22 carbon atoms and the alkenyl radicals have 2-22 carbon atoms, which are uninterrupted or interrupted by a carbonyloxy or oxycarbonyl group, where the repeating units in square brackets are distributed randomly and/or in blocks in the polymers and where both the repeating units indicated by x and y are identical or different and where the amino acids are α- and/or β-linked.

Aryl is understood as meaning aromatic hydrocarbons such as phenyl and naphthyl, in particular phenyl. In the substituted aryl radicals indicated, 1 to all replaceable hydrogen atoms are replaced by identical or different substituents. The aryl radicals are preferably mono- or disubstituted. Said alkyl and alkenyl radicals can be either straight-chain or branched. The biologically inactive steroid alcohols are preferably bonded via their OH group. A preferred steroid alcohol is cholesterol. Said amino acids for $R^1$ are preferably naturally occurring amino acids such as Tyr, Ala, Ser or Cys, particularly preferably Tyr and Ala. They can be bonded either via their $NH_2$ or via their COOH function.

The invention also relates to the process for the preparation of the abovementioned polyamides and also their use in a mixture with other biotolerable polyamides, particularly in combination with biologically active substances, as a degradable active compound depot preparation having controlled delivery of active compound.

The invention is described in detail in the following.

Aspartic acid and/or glutamic acid, which can be reacted to the corresponding polyanhydroaminodicarboxylic acids II in a polycondensation reaction, are employed as aminodicarboxylic acids. As a result of partial reaction with one or more compounds of the formulae III and/or IV and/or NH₃

HO—R¹ (III)

H₂N—(CH₂)ₘ—OH (IV), in which m and R¹ are defined as above for formula I, an α,β-poly-D,L-amino acid ester or an α,β-poly-D,L-amino acid amide of the formula VIII

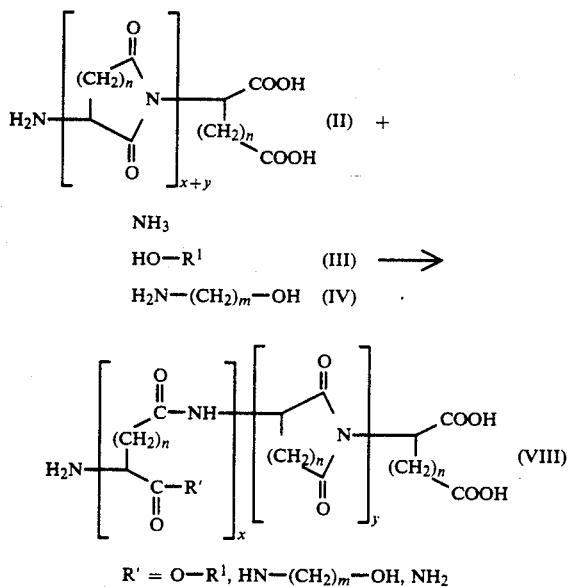

is obtained.

It is essential to the invention in this reaction that the polyanhydroaminodicarboxylic acid (II) is only partially converted into the open-chain derivatives. The proportion of unopened anhydroaminodicarboxylic acid units is 0.1 to 99.9%, preferably 10 to 90%, particularly preferably 60 to 80% (the percentage data relate to the total number of repeating units in the entire polymer). Depending on which side the anhydroaminodicarboxylic acid ring is opened in the reaction described above, α- or β-linked amino acids are obtained. Preferably employed compounds of the formulae III and IV are: 2-aminoethanol, 3-aminopropanol, 2-aminopropanol, alcohols having 1-18 carbon atoms, in particular methanol, ethanol, isoamyl alcohol, tertiary butyl alcohol and isopropyl alcohol.

A process for the preparation of α,β-poly-(2-hydroxyethyl)-DL-aspartamide (PHEA) (formula I; y=0; R=NH—CH₂—CH₂—OH) is described by P. Neri, G. Antoni, F. Benvenuti, F. Cocola, G. Gazzei, in J. Med. Chem. Vol. 16, 893 (1973). A general procedure for the preparation of PHEA can be found in P. Neri, G. Antoni, Macromol. Synth. Vol. 8, 25. Reference is expressly made here to this literature reference. The reaction takes place in high yield to give a product having a high degree of purity. The analogous poly-aspartic acid derivative-co-succinimide compounds of the formula VIII (n=1) can be prepared in the same way by sub-stoichiometric use of NH₃ and/or compounds of the formulae III and/or IV.

Another, more involved process, as is described in U.S. Pat. No. 4,356,166, has to be used for the preparation of pure poly-(hydroxyalkyl)-L-glutamine. In this process, the COOH group in the γ-position of L-glutamic acid is first protected by esterification with benzyl alcohol. This γ-benzyl glutamate is then reacted with phosgene to give an N-carboxyanhydride, which is polymerized in an inert solvent after adding triethylamine, poly-γ-(benzyl) L-glutamate being obtained. The protecting group is removed either by adding an HCl/HBr mixture to the free poly-α-L-glutamic acid or else in the presence of hydroxyalkylamines to give the analogous poly-α-(hydroxyalkyl)-L-glutamines. A general procedure for the preparation of poly-α-(hydroxypropyl)-L-glutamine is found in U.S. Pat. No. 4,356,166, to which reference is expressly made here. In the same manner, the analogous compounds of the formula VIII (n=2) can also be prepared by use of NH₃ and/or compounds of the formulae III and/or IV.

Compared to the complicated preparation of pure polyglutamic acid and its derivatives, glutamic acid can additionally be incorporated up to high proportions in the simple condensation of aspartic acid by means of phosphoric acid to give polyanhydroaspartic acid-co-glutamic acid.

The polyamino acid amide-co-anhydrodicarboxylic acids of the formula VIII (R'=HN—(CH₂)ₘ—OH) can then be reacted, if necessary, in the following reaction step with one or more different, biologically inactive compounds of the formulae V and/or VI and/or VII

X—R¹ (V)

$$X-\underset{\underset{O}{\|}}{C}-R^1 \quad (VI)$$

$$X-\underset{\underset{O}{\|}}{C}-OR^1 \quad (VII)$$

to give further polyaminodicarboxylic acid-co-AHADA derivatives according to the invention. In this connection, X is a leaving group which enables a mild esterification of the polymer alcohol group. Chlorine, bromine, iodine, imidazolides, anhydrides or hydroxyl are preferred, in particular chlorine.

The reaction with the compounds of the formula type V, VI or VII can be carried out either using a single compound of this type or using any desired combinations of these compounds or, alternatively, using compounds which have different R¹ radicals, for example in the manner of their branching, in particular differing in their chain length.

The last-mentioned polymer-analogous alkylation or acylation is carried out by known methods of organic chemistry. It proceeds selectively at the hydroxyl function (formula VIII, R'=HN—(CH₂)ₘ—OH) to give ethers, esters or carbonates, without attacking other functions in the starting polymer. The Einhorn variant of the Schotten-Baumann acylation in the presence of pyridine is particularly suitable. In this acylation, very high degrees of derivatization (greater than 70%) are achieved under mild conditions.

The molecular weight of the polymers according to the invention is 200 to 100,000, preferably 3,000 to 70,000.

Compounds of the formula type V are commercially available or, if not commercially available, can be synthesized in a simple manner by methods known from the literature.

The chloroformic acid esters (formula VII) are obtained by reaction of phosgene with the appropriate biologically inactive, physiologically acceptable aromatic, araliphatic, aliphatic or cycloaliphatic alcohols, in particular unbranched alcohols. Those alcohols are particularly preferably employed which have an even number of carbon atoms. The chloroformylated steroids are also obtained in this manner. Thus, in principle, all biologically inactive steroids which have reactive hydroxyl groups are accessible. Examples which may be mentioned here are: cholesterol, cholestanol, coprostanol, ergosterol, sitosterol or stigmasterol.

The acid chlorides (formula VI) which can also be employed are obtained, for example, from the corresponding carboxylic acids by reaction with phosphorus trichloride, phosphorus pentachloride, oxalyl chloride or thionyl chloride.

Compounds of the formula type V, VI or VII in which an alkyl chain is interrupted by an oxycarbonyl or carbonyloxy group are prepared, for example, by reaction of cyclic dicarboxylic acid anhydrides with alcohols. The dicarboxylic acid monoesters obtained in this manner are then reacted to give the corresponding acid chlorides analogously to the carboxylic acids described above, for example using oxalyl chloride.

The hydrophobicity of the polyaminodicarboxylic acid-co-AHADA derivatives—and thus the residence time of an implant prepared from these in the organism—can be adjusted within wide limits both via the number of carbon atoms in the alkylation or acylation agent and via the degree of substitution and the content of unopened AHADA.

However, an exact indication of the relation chain length/AHADA content/degradation time in vitro/vivo is only possible with difficulty, as apart from the chain length and the AHADA content, the degradation time is still dependent on a large number of other parameters; for example on the particle size and distribution, the preparation method, for example, for microspheres, the porosity of the microspheres, the temperature or the degradation medium. However, by means of simple routine tests within the bounds of the disclosure, it is possible for the person skilled in the art to achieve the desired degradation time.

The degree of substitution in the compounds VIII ($R'=HN-(CH_2)_m-OH$ can be modified via the stoichiometry of the substances employed in the alkylation or acylation reaction, but should preferably be kept within the bounds of the maximum yield (greater than 70%), i.e. an as large as possible percentage of the substitutable OH groups in the polymer structure (formula VIII; $R'=HN-(CH_2)_m-OH$ should be esterified. If a lower degree of substitution is desired, the concentration of the alkylation or acylation agent is correspondingly reduced with respect to the polymer.

During the degradation of these polyamides in vivo, a) the imide rings in the main polymer chain are cleaved and b) the reactive side groups in the polyamides are hydrolyzed again and the corresponding biologically inactive carboxylic acids or alcohols and poly-(hydroxyalkyl) aminodicarboxylic acid and, if provided for the purpose of better water-solubility, to a small extent oligoaminodicarboxylic acid sequences are formed. Ideally, this degradation under physiological conditions should exclusively produce endogenous fragments known in their high biotolerability and which are metabolized by natural metabolic means or excreted by the kidneys owing to their water-solubility. The biotolerable carboxylic acids and alcohols include those having 6–22 carbon atoms in the alkyl moiety, in particular those having an even number of carbon atoms.

The presence of $\alpha$- and $\beta$-peptide bonds in the D- and L-form in the $\alpha,\beta$-poly-DL-aminodicarboxylic acid amide-co-AHADA derivatives employed prevents the formation of organized structures (for example folded sheet or helix areas) in the polymer, which influence the biodegradation in an unforeseeable manner.

Some of the polyamides according to the invention are thermoplastic and are therefore suitable for the preparation of active compound depot forms by various methods, such as, for example, by compression, extrusion, precipitation, spraying, etc.

Implantable particles, in particular microcapsules and microspheres and also macroscopic shaped articles formed by compaction, of any desired geometry, in particular tablets and rods, can be prepared from the polyamides according to the invention by known methods.

The excellent solubility of the polymers according to the invention in many organic solvents also enables the formation of microspheres by dripping from a solvent having a high melting point into a condensed cold gas, for example liquid nitrogen, absolutely round particles being formed by the Leidenfrost's phenomenon. The high-melting and water-miscible solvent is dissolved out by transfer of the microspheres to water and the polymer is precipitated at the same time, the spherical shape of the polyamide microspheres being retained.

If, in addition to a high melting point, the organic solvent used at the same time has a low boiling point, this drop formation process is further simplified in that the solvent, for example tert. butanol, can be directly removed in a mild manner and without active compound losses by means of freeze-drying of the microspheres obtained by dropwise addition to liquid nitrogen.

The solubility of the polyamides according to the invention has a particularly advantageous effect in many solvents which are also physiologically tolerable, for example alcohols, in the processing to give microspheres by means of spray-drying. Thus, the use of toxicologically hazardous halogenated hydrocarbons, such as are necessary for the spray-drying of biodegradable polyesters, can be dispensed with in the case of the polyamides according to the invention. Moreover, their solubility also permits the preparation in alcohol/water mixtures of monolithic, active compound-containing microspheres, as in this case polymer and active compound can be sprayed from a molecularly disperse form.

The polyamides according to the invention can also be employed as mixtures and in mixtures with other biodegradable and/or biotolerable polymers (for example ®Pluronic F68, PHEA, dextrans, polyethylene glycols, hydroxyethylstarch and other degradable or excretable polysaccharides) or physiologically acceptable auxiliaries (for example polymer plasticizers).

Degradation tests in vitro using the polyamides according to the invention have shown that the degradation rate can be controlled both by means of the functional side groups and by means of the number of AHADA units.

The invention is described in detail in the following examples. Percentage data relate to the weight, unless stated otherwise.

EXAMPLE 1

Preparation of polyanhydroaspartic acid-co-$\alpha,\beta$-(hydroxyethyl)-D,L-aspartamide (70:30)

10 g (103 mmol) of polyanhydroaspartic acid are dissolved in about 40 ml of DMF, if necessary with gentle warming. 1.83 ml (30 mmol) of freshly distilled 2-aminoethanol are added dropwise to this solution and it is stirred overnight at room temperature. The reaction mixture is precipitated in butanol and the precipitate is washed several times with dry acetone. Drying is carried out in vacuo at elevated temperature. The white, water-soluble product is formed to approximately 100% and is tested for residues of DMF and butanol by NMR spectroscopy. The molar ratio of polyanhydroaspartic acid to aminoethanol employed corresponds approximately to the copolymer composition.

EXAMPLE 2

Preparation of n-butyl 4-chloro-4-oxobutyrate

Excess thionyl chloride and a few drops of DMF are added to monobutyl succinate. The reaction starts with evolution of gas. The mixture is stirred overnight with the exclusion of moisture and the excess thionyl chloride is then removed by distillation at normal pressure. The crude product which remains is fractionally distilled at 0.05 mbar and the pure product is obtained at about 70° C. In the IR-spectroscopic characterization, the product has bands at 1,800 cm$^{-1}$ (acid chloride) and 1,740 cm$^{-1}$ (ester) of equal intensity.

EXAMPLE 3

Preparation of polyanhydroaspartic acid-co-$\alpha,\beta$-(butyloxycarbonylpropionyloxyethyl)-D,L-aspartamide (70:30)

6 g of polyanhydroaspartic acid-co-$\alpha,\beta$-(hydroxyethyl)-D,L-aspartamide ($\hat{=}$16 mmol of hydroxyethyl groups), prepared as described in Example 1, are dissolved in 100 ml of dry N,N-dimethylformamide (DMF). After adding 4 g (50 mmol) of pyridine, the mixture is cooled to 0° C. and 4.8 g (25 mmol) of n-butyl 4-chloro-4-oxobutyrate (preparation Ex. 2) are added with stirring in the course of 15 minutes. The mixture is stirred overnight and precipitated in 0.5 l of ether. The precipitated product is filtered off with suction, washed with ether, acetone, water, acetone and ether. About 8 g of a white polymer having a degree of substitution of approximately 100% (checkable by NMR spectroscopy) are obtained. The resulting polymer is soluble, for example, in acetonitrile containing a trace of DMSO, and in DMSO or DMF.

EXAMPLE 4

Preparation of polyanhydroaspartic acid-co-$\alpha,\beta$-(nonylcarbonyloxyethyl)-D,L-aspartamide (50:50)

6 g of a polyanhydroaspartic acid-co-$\alpha,\beta$-(hydroxyethyl)-D,L-aspartamide (50:50) ($\hat{=}$24 mmol of hydroxyethyl groups), which was prepared from polyanhydroaspartic acid (MW=14,000) and 2-aminoethanol (molar ratio 2:1) analogously to Example 1, are dissolved in 100 ml of dry DMF, 8 g (100 mmol) of dry pyridine are added and the mixture is cooled to 0° C. 9.6 g of distilled decanoyl chloride are slowly added dropwise and the mixture is further processed analogously to Example 3. About 8 g of a white, completely substituted polymer (NMR checking) are obtained, which is soluble, for example, in dichloromethane and THF each containing a trace of DMSO or in methanol/dichloromethane mixtures.

EXAMPLE 5

Preparation of polyanhydroaspartic acid-co-$\alpha,\beta$-(nonylcarbonyloxyethyl)-D,L-aspartamide of differing copolymer composition and different molecular weight.

Differing polyanhydroaspartic acid-co-$\alpha,\beta$-(hydroxyethyl)-D,L-aspartamides, inter alia of the composition 70:30, 50:50 and 30:70, were prepared from polyanhydroaspartic acids of different molecular weights (MW=7,000; about 13,000; 30,000) analogously to Example 1 and reacted with decanoyl chloride, as described in Example 4, to give the corresponding polyanhydroaspartic acid-co-$\alpha,\beta$-(nonylcarbonyloxyethyl)-D,L-aspartamides.

a)—Polyanhydroaspartic acid-co-$\alpha,\beta$-(nonylcarbonyloxyethyl)-D,L-aspartamide (70:30) from polyanhydroaspartic acid (MW=7,000); characterized by NMR b)—Polyanhydroaspartic acid-co-$\alpha,\beta$-(nonylcarbonyloxyethyl)-D,L-aspartamide (70:30) from polyanhydroaspartic acid (MW=14,000); characterized by NMR c)—Polyanhydroaspartic acid-co-$\alpha,\beta$-(nonylcarbonyloxyethyl)-D,L-aspartamide (70:30) from polyanhydroaspartic acid (MW=30,000); characterized by NMR c)—Polyanhydroaspartic acid-co-$\alpha,\beta$-(nonylcarbonyloxyethyl)-D,L-aspartamide (30:70) from polyanhydroaspartic acid (MW=12,000); characterized by NMR Microparticles of these products differ distinctly in solubility, consistency, degradation behavior and active compound release (Examples 12 and 13)

EXAMPLE 6

Preparation of polyanhydroaspartic acid-co-$\alpha,\beta$-(octyloxycarbonyloxyethyl)-D,L-aspartamide (70:30)

6 g of polyanhydroaspartic acid-co-$\alpha,\beta$-(hydroxyethyl)-D,L-aspartamide (70:30) ($\hat{=}$16 mmol of hydroxyethyl groups), prepared as described in Example 1 from polyanhydroaspartic acid (MW=37,000) and aminoethanol, are reacted with 4.8 g (25 mmol) of octyl chloroformate analogously to Example 3 and also worked up correspondingly. About 8 g of a white, completely substituted polymer are obtained, which is soluble in THF or methanol/dichloromethane mixtures.

EXAMPLE 7

Preparation of polyanhydroaspartic acid-co-$\alpha,\beta$-(nonylcarbonyloxyethyl)-co-$\alpha,\beta$-(hydroxyethyl)-D,L-aspartamide (60:20:20)

6 g of polyanhydroaspartic acid-co-$\alpha,\beta$-(hydroxyethyl)-D,L-aspartamide (60:40) ($\hat{=}$20 mmol of hydroxyethyl groups), which was prepared from polyanhydroaspartic acid and 2-aminoethanol (molar ratio 6:4) analogously to Example 1, are reacted with 2.3 g of decanoyl chloride ($\triangleq$ 12 mmol) analogously to Example 3. As a result of the incomplete conversion (comparatively small excess of acid chloride), only half of the free OH groups are esterified. About 7 g of a white polymer are formed. Despite the rapid solubilization and the rapid degradation associated therewith in comparison to the microparticles of polymers of Examples 3–6, microparticles of this substance have a similar solid consistency in water and are easily suspensible.

EXAMPLE 8

Preparation of polyanhydroaspartic acid-co-α,β-(oleyloxyethyl)-D,L-aspartamide (10:90)

6 g of polyanhydroaspartic acid-co-α,β-(hydroxyethyl)-D,L-aspartamide (10:90) ($\triangleq$ 40 mmol of hydroxyethyl groups), prepared analogously to Example 1 using a molar ratio of polyanhydroaspartic acid to 2-aminoethanol such as 1:9, are reacted with 20 g of distilled oleyol chloride analogously to Example 3. The heterogeneous reaction mixture becomes homogeneous as a result of the addition of dichloromethane. It is precipitated twice in methanol cooled to −20° C. The yellowish-colored polymer is thermoplastic.

EXAMPLE 9

Preparation of rod-shaped implants ("rods")

An intimate mixture of pulverulent, thermoplastically processable polymers (substance from Example 8), additives and active compound(s) is heated to above the softening point in a suitable device, for example an extruder for thermoplastics, a plastic material being formed. Additives and active compound(s) are homogeneously dispersed in the softened polymer by kneading and the polymer/active compound suspension obtained is forced through a nozzle of suitable diameter (>0.5 mm). On cooling, the strand of the extruded polymer/active compound suspension solidifies to give a solid rod-shaped aggregate whose active compound content is determined by its length and its diameter.

EXAMPLE 10 a) Preparation of microspheres 40 mg of polyanhydroaspartic acid-co-α,β-(nonylcarbonyloxyethyl)-D,L-aspartamide (50:50) from Example 4 are dissolved in 1 ml of methylene chloride/methanol (volume ratio 50:1). 10 mg of buserelin are added to the solution and dispersed using ultrasound. The dispersion is introduced with stirring (800 rpm) into a beaker containing 60 ml of 0.1% strength aqueous polyvinyl alcohol solution (®Mowiol 28-99) which is saturated with 0.3 ml of methylene chloride/methanol (50:1).

After 5 minutes, the contents are added to a beaker containing 200 ml of water and stirred for 30 minutes (200 rpm). The supernatant water is decanted off and the microspheres are lyophilized (diameter after lyophilization: 20–90 μm).

b) Preparation of microspheres 80 mg of polyanhydroaspartic acid-co-α,β-(octylcarbonyloxyethyl)-D,L-aspartamide (70:30) from Example 6 are dissolved in 1 ml of dimethyl sulfoxide at 50° C. and 20 mg of hydroxypropylcellulose (®Klucel M.) are added. The solution of the two polymers is added dropwise using a needle (disposable syringe, external needle diameter 0.6 mm) to a receiver of liquid nitrogen (100 ml).

The resulting microspheres are transferred to 200 ml of water and residual solvent is extracted for 2 hours. Excess water is removed by decantation and the microspheres are lyophilized (diameter after lyophilization: 1–2 μm).

c) 3.76 g of polyamide according to Example 5 c) are dissolved in 195 ml of dichloromethane (0.25% DMSO) with warming and the mixture is combined with a solution of 240 mg of buserelin in 5 ml of water. The mixture is sprayed into a spray-drier to give microspheres.

d) 3.76 g of polyamide according to Example 5 d) are dissolved in 195 ml of dichloromethane (0.25% DMSO) with warming and the mixture is combined with a solution of 240 mg of buserelin in 5 ml of water. The mixture is sprayed into a spray-drier to give microspheres.

e) 3.76 g of polyamide according to Example 6 are dissolved in 195 ml of dichloromethane (0.25% DMSO) with warming and the mixture is combined with a solution of 240 mg of buserelin in 5 ml of water. The mixture is sprayed into a spray-drier to give microspheres.

f) 3.76 g of polyamide according to Example 4 are dissolved in 195 ml of dichloromethane (0.25% DMSO) with warming and the mixture is combined with a solution of 240 mg of buserelin in 5 ml of water. The mixture is sprayed into a spray-drier to give microspheres.

g) 3.76 g of polylactide glycolide (50:50) (PLGA 50:50) (Boehringer Ingelheim) are dissolved in 195 ml of dichloromethane (0.25% DMSO) with warming and the mixture is combined with a solution of 240 mg of buserelin in 5 ml of water. The mixture is sprayed into a spray-drier to give microspheres.

h) 3.76 g of polyamide according to Example 5 d) are dissolved in 195 ml of tetrahydrofuran (0.25% DMSO) with warming and the mixture is combined with a solution of 240 mg of buserelin in 5 ml of water. The solution is sprayed into a spray-drier to give microspheres.

EXAMPLE 11

Water absorption

The water absorption of the polyamides after storage at 92% relative atmospheric humidity for 74 h is 8–10% by weight for polyanhydroaspartic acid-co-α,β-(nonylcarbonyloxyethyl)-D,L-aspartamide (70:30) from polyanhydroaspartic acid (MW=30,000) according to Example 5 c) and for polyanhydroaspartic acid-co-α,β-(octyloxycarbonyloxyethyl)-D,L-aspartamide (70:30) from polyanhydroaspartic acid (MW=37,000) according to Example 6.

EXAMPLE 12

Polymer degradation 4 samples of 120 mg of polymer each are incubated at 37° C. in 30 ml each of a phosphate buffer solution composed of 2.05 mmol of $Na_2HPO_4$, 4.5 mmol of $NaH_2PO_4$ and 7.8 mmol of $NaN_3$ (pH 7.4) in closed glass flasks (50 ml). The decrease in weight of the polymer samples was measured by filtering the buffer solution containing incubated polymer through a tared glass frit, drying the residue in vacuo over phosphorus pentoxide for 24 h and determining the decrease in weight.

Series of examples with polyanhydroaspartic acid-co-α,β-(nonylcarbonyloxyethyl)-D,L-aspartamides of differing copolymer composition (x:y) and different molecular weights (from Examples 4 and 5).

| from Ex. No. | X:Y | | MW* | Weight decrease (%) after | | | |
|---|---|---|---|---|---|---|---|
| | | | | 2 | 5 | 10 | 20 days |
| 5c | 70 | 30 | 30,000 | 6 | 20 | 45 | 70 |
| 5b | 70 | 30 | 14,000 | 15 | 40 | 65 | 95 |
| 4 | 50 | 50 | 14,000 | 10 | 35 | 58 | 88 |
| 5d | 30 | 70 | 12,000 | 8 | 15 | 30 | 50 |

*value for the polyanhydroaspartic acid employed determined by viscometry

EXAMPLE 13

Active compound release (release of buserelin) after 24 h (initial burst)

20 mg of microparticles having a 6% loading of buserelin were weighed into 10 ml glass flasks and 5 ml of lecithin-containing buffer solution (2.91 g of $Na_2HPO_4$, 0.54 g of $NaH_2PO_4$, 0.1 g of $NaN_3$, 6.33 g of $NaHCO_3$ and 10 g of egg lecithin made up to 1 l $H_2O$) were added. The samples were stirred using magnetic stirrer bars in such a way that the microparticles were kept in suspension and no particles were able to collect on the surface or the vessel walls and larger aggregates were unable to be formed with microparticles of tacky consistency. After 24 hours, the samples were filtered and the buserelin content in the filtrate was determined by means of HPLC.

| Polymer | Microspheres from Ex. | MW of the PSI employed | Buserelin release after 24 h |
|---|---|---|---|
| *PLGA (50:50) | 10 g) | | 50–60% |
| PSI-co-HEA C10 (70:30) | 10 c) | 30,000 | 10–15% |
| PSI-co-HEA-C1C8 | 10 e) | 37,000 | 10–15% |
| PSI-co-HEA C10 (50:50) | 10 f) | 14,000 | 40% |
| PSI-co-HEA C10 (30:70) | 10 d) | 12,000 | 60–70% |

*Comparison example
PSI = polyanydroaspartic acid
HEA = hydroxyethylamide

We claim:

1. A polyaminodicarboxylic acid-co-anhydroaminodicarboxylic acid derivative of the Formula I

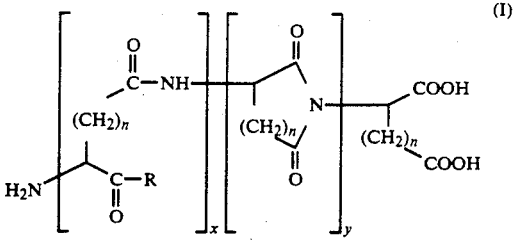

in which
n is 1 or 2,
x is 1 to 500,
y is 1 to 500, where
x+y is 2 to 1000 and
R is $NH-R^2$, in which $R^2$ is $(CH_2)_m-O-C(O)-R^1$ and m is 2 to 6 and $R^1$ is H, aryl, aralkyl, arylalkenyl, alkyl or $C_3-C_8$-cycloalkyl, where aryl is unsubstituted or substituted by $C_1-C_4$-alkyl, $C_2-C_4$-alkenyl, $C_1-C_4$-alkylcarbonyloxy, $C_1-C_4$-alkoxycarbonyl, $C_1-C_4$-alkoxy or hydroxyl, where the alkyl radicals for $R^1$ have 1-22 carbon atoms and the alkenyl radicals have 2-22 carbon atoms, which are uninterrupted or interrupted by a carbonyloxy or oxycarbonyl group, or $R^1$ is the monovalent residue of a biologically inactive steroid alcohol or an amino acid,
where the repeating units in square brackets are distributed randomly or in blocks or both randomly and in blocks in the polymers and where both the repeating units indicated by x and y are identical or different and where the amino acids are α- or β-linked or both α- and β-linked.

2. A polyaminodicarboxylic acid-co-anhydroaminodicarboxylic acid derivative of the formula I as claimed in claim 1, in which
m is 2 and
$R^1$ is H, aryl, aralkyl, alkyl or $C_5-C_6$-cycloalkyl, where the aryl radicals contain 1-22 carbons atoms.

3. A polyaminodicarboxylic acid-co-anhydroaminodicarboxylic acid derivative of the Formula I as claimed in claim 1, in which R is $NH-R^2$, $R^2$ is $(CH_2)_m-O-C(O)-R^1$ and $R^1$ is alkyl.

* * * * *